(12) United States Patent
Kanner et al.

(10) Patent No.: US 6,382,417 B2
(45) Date of Patent: May 7, 2002

(54) SURGICAL NEEDLE IMMOBILIZATION DEVICE

(75) Inventors: Rowland W. Kanner, Guntersville; Larry Lee Young, Arab, both of AL (US)

(73) Assignee: Atrion Medical Products, Inc., Arab, AL (US)

( * ) Notice: Subject to any disclaimer, the term of this patent is extended or adjusted under 35 U.S.C. 154(b) by 0 days.

(21) Appl. No.: 09/813,703

(22) Filed: Mar. 21, 2001

Related U.S. Application Data (60) Provisional application No. 60/190,821, filed on Mar. 21, 2000.

(51) Int. Cl.[7] .......................... B65D 85/24; B65D 83/10
(52) U.S. Cl. ................ 206/366; 220/23.4; 604/110
(58) Field of Search ................ 206/363–370, 206/372, 380; 29/240, 240.5; 220/23.4; 604/110, 192; 53/402

(56) References Cited

U.S. PATENT DOCUMENTS

| | | | |
|---|---|---|---|
| 4,928,917 A | | 5/1990 | Wolf |
| 4,981,476 A | | 1/1991 | Aichlmayr et al. |
| 4,986,811 A | | 1/1991 | Thead et al. |
| 5,417,659 A | | 5/1995 | Gaba |
| 5,469,964 A | * | 11/1995 | Bailey .................. 206/364 |
| 5,533,974 A | | 7/1996 | Gaba |
| 5,584,809 A | * | 12/1996 | Gaba .................. 604/110 |
| 6,123,193 A | * | 9/2000 | Vojtasek et al. ........... 206/366 |

* cited by examiner

*Primary Examiner*—Luan K. Bui
(74) *Attorney, Agent, or Firm*—Trexler, Bushnell, Glanglorgi, Blackstone & Marr, Ltd.

(57) ABSTRACT

A multiple capacity surgical needle immobilization safety device is provided for use in disposal of needles during medical treatment. The device can be included in a procedure kit or trays where several needles and cannulas, up to five per tray, are provided as a set to be used sequentially in performing a specific procedure such as spinal block or other anesthesia.

38 Claims, 8 Drawing Sheets

SURGICAL NEEDLE IMMOBILIZATION DEVICE

The present invention claims domestic priority of U.S. Provisional Application Ser. No. 60/190,821, filed on Mar. 21, 2000 and entitled "Surgical Needle Immobilization Device".

BACKGROUND OF THE INVENTION

This invention is generally directed to a multiple capacity surgical needle immobilization safety device for use in disposal of needles during medical treatment.

OSHA guidelines and various state laws have placed pressure upon the providers of medical sharps and needle manufacturers, as well as the medical care providers, to take steps to provide disposable sharps products in a manner that would help reduce needle sticks and other sharps injuries to eliminate health care workers exposure to blood borne pathogens. Some "safety syringes" are currently being sold, but they are expensive, can not cover all needle lengths/gauge options and some are confusing to use. Additionally, there are procedures where the needle is used alone (not attached to a syringe) or may be used with a reusable syringe body, in which case the sharp must be protected or safely immobilized until the sharp can be disposed of in a sharps container. Procedure trays requiring multiple needles must make the isolation of the contaminated sharps convenient or the health care worker will not spend time or have time during the procedure to exercise proper safety precautions.

Some needle locking safety devices which are currently being sold will immobilize one needle upon its insertion into the device. An example of such a device is the Noved "sharp end foil" or Needle Lock. Applicant believes that this Noved device is made by Devon Industries Inc. under U.S. Pat. No. 5,417,659. While these prior art needle locking safety devices perform the intended function, they can be inconvenient to use because the needle locking safety device must be set up, properly oriented and arrayed in a convenient location, somewhere in a crowded work space by the user before they can be employed. These prior art needle locking safety devices can become unstable if loaded with a large syringe and may fall over, contaminating the sterile tray or its contents, or even end up on the floor. When time comes for disposal in the sharps container, the needles and syringes with these prior art needle locking safety devices must be gathered up one-by-one from wherever they come to rest and carried to the sharps container. Often the health care workers will toss the whole tray into the sharps container after throwing these used items into it, wasting space in the sharps container. Finally, these prior art needle locking safety devices can take up a lot of valuable space when delivered in the procedure tray and in the sharps disposal container even if disposed of alone. In addition, the prior art needle locking safety devices are not inexpensive.

The present invention provides a multiple capacity surgical needle immobilization safety device for use in medical treatment. This surgical needle immobilization safety device can be included in a procedure kit or trays where several needles and cannulas, up to five per tray, are provided as a set to be used sequentially in performing a specific procedure such as spinal block or other anesthesia. Other features and advantages of the surgical needle immobilization safety device of the present invention will become clear upon a reading of the attached specification in combination with a study of the drawings.

OBJECTS AND SUMMARY OF THE INVENTION

A general object of the present invention is to provide a novel multiple capacity surgical needle immobilization safety device which will accept needles from the largest twenty-two gauge procedure needles to the smallest twenty-seven gauge needles.

An object of the present invention is to provide a novel multiple capacity surgical needle immobilization safety device which is delivered in the procedure kit tray, set up and ready for use.

Another object of the present invention is to provide a novel multiple capacity surgical needle immobilization safety device which is easily and quickly assembled and is easy to use.

Briefly, and in accordance with the foregoing, the present invention discloses a novel multiple capacity surgical needle immobilization safety device which is provided for use in disposal of needles during medical treatment. The device will accept needles from the largest twenty-two gauge procedure needles to the smallest twenty-seven gauge needles. The device can be included in a procedure kit or trays where several needles and cannulas, up to five per tray, are provided as a set to be used sequentially in performing a specific procedure such as spinal block or other anesthesia.

BRIEF DESCRIPTION OF THE DRAWINGS

The organization and manner of the structure and operation of the invention, together with further objects and advantages thereof, may best be understood by reference to the following description, taken in connection with the accompanying drawings, wherein like reference numerals identify like elements in which.

DETAILED DESCRIPTION OF THE ILLUSTRATED EMBODIMENT

While the invention may be susceptible to embodiment in different forms, there is shown in the drawings, and herein will be described in detail, specific embodiments with the understanding that the present disclosure is to be considered an exemplification of the principles of the invention, and is not intended to limit the invention to that as illustrated and described herein.

Figure 4:
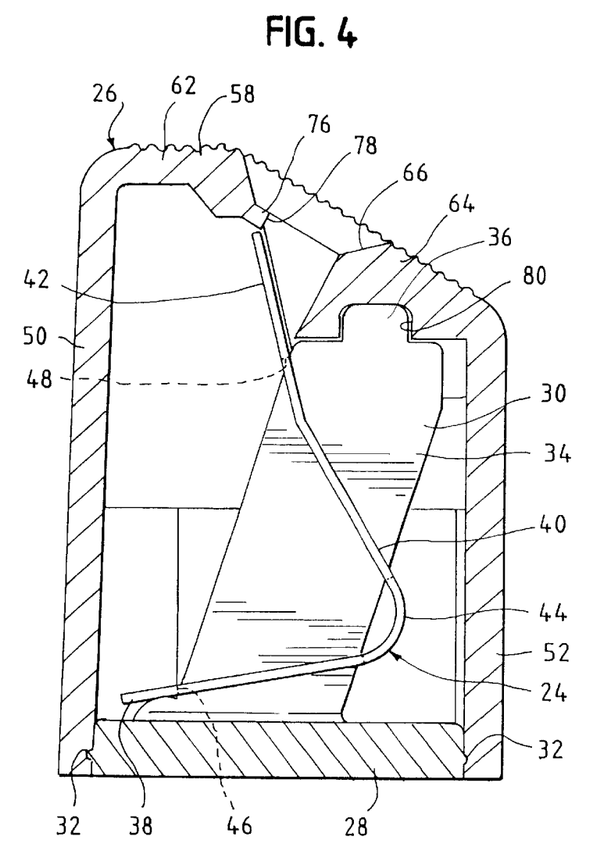
FIG. 4 is a cross-sectional view of the device through line 4—4 of FIG. 1.
Figure 5:
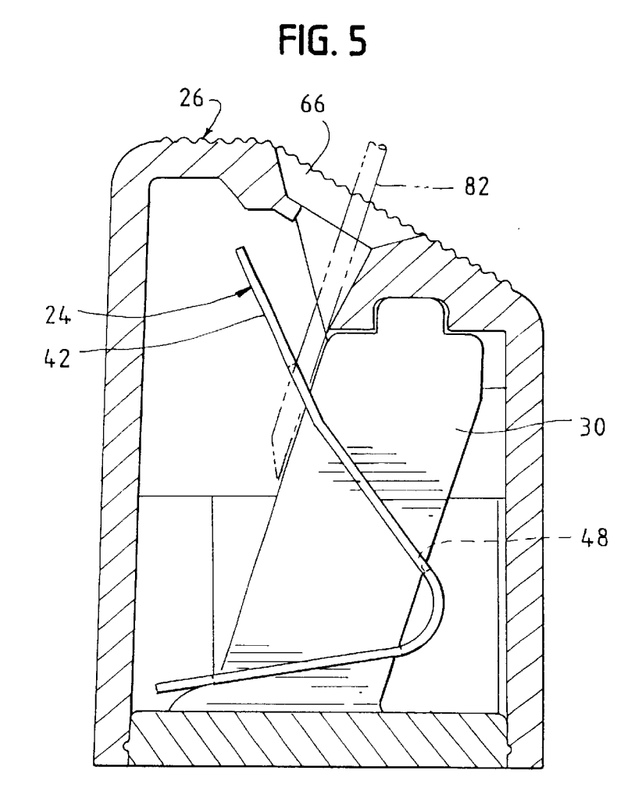
FIG. 5 is a cross-sectional view of the device showing a needle in phantom line which is inserted therein.
Figure 6:
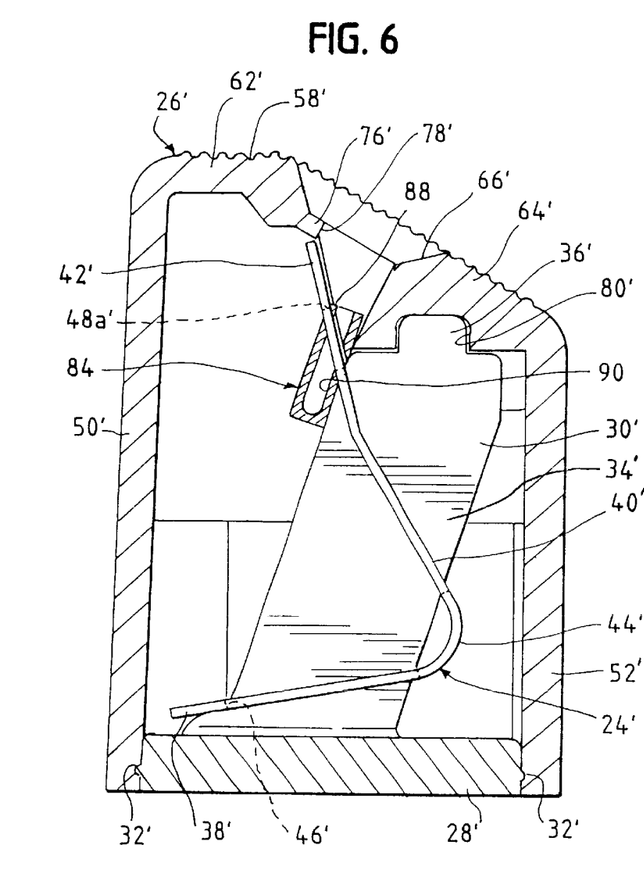
FIG. 6 is a cross-sectional view of a device which incorporates the features of a second embodiment of the present invention.
Figure 7:
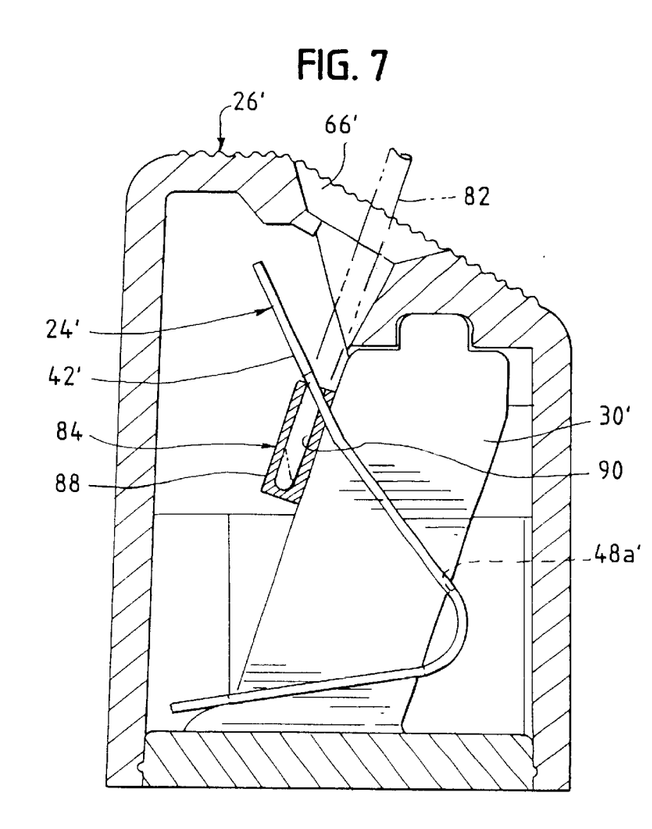
FIG. 7 is a cross-sectional view of the second embodiment of the device showing a needle in phantom line which is inserted therein.

The present invention provides a novel multiple capacity surgical needle immobilization safety device 20, 20', 20". A first embodiment of the device 20 is shown in FIGS. 1–5; a second embodiment of the device 20' is shown in FIGS. 6 and 7; a third embodiment of the device 20" is shown in FIGS. 8–12.

The multiple capacity surgical needle immobilization safety device 20, 20', 20" of the present invention will accept needles from the largest twenty-two gauge procedure needles to the smallest twenty-seven gauge needles. The present device 20, 20', 20" also is conveniently delivered in the procedure kit tray, set up and ready for use. The device 20, 20', 20" occupies little more space than the foam needle stick pad currently used in the procedure kit, and is made to be packed by the procedure kit supplier, into a small receiving pocket where the foam pad once resided, which keeps it upright. Upon completion of the procedure, the device 20, 20', 20" can be removed from the tray. The device 20, 20', 20" is easily and quickly assembled and is easy to use.

Attention is invited to the first embodiment of the invention shown in FIGS. 1–5. The device 20 includes a lower member 22, a plurality of spring clips 24 and an upper member 26. The lower and upper members 22, 26 form a housing when coupled together.

Figure 3:
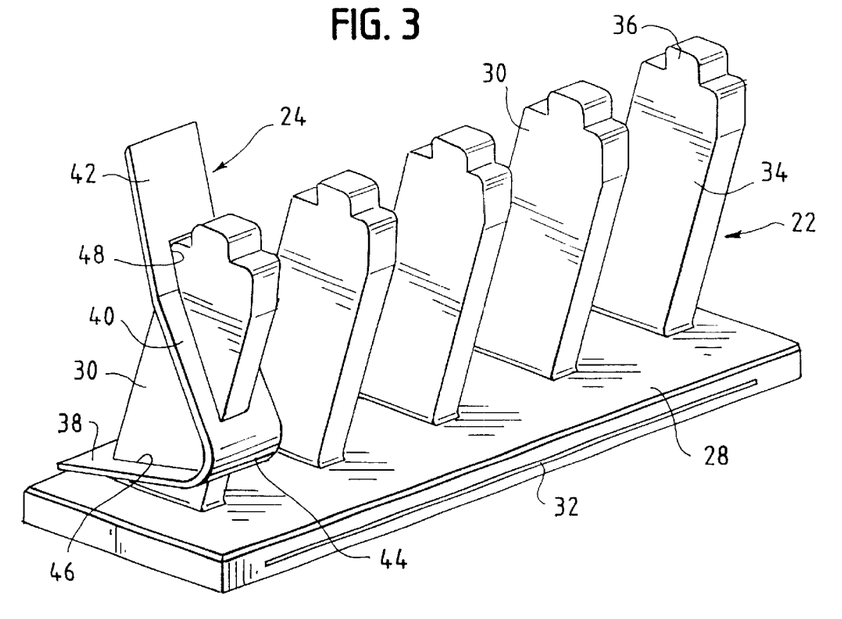
FIG. 3 is a perspective view of a lower member which includes a plurality of posts, one of the posts having a clip mounted thereon.

As shown in FIG. 3, the lower member 22 is formed of a suitable material, such as plastic. The lower member 22 includes a horizontal base 28 and a plurality of posts 30. The posts 30 extend upwardly from the base 28 and are spaced apart from each other along the length of the base 28. As shown in the drawings, the base 28 is rectangular and five posts 30 are provided thereon. An elongated rib 32 is provided along each side of the base 28 and extends substantially the entire length thereof. Each post 30 extends upwardly from the base 28 at an angle relative thereto and is formed from a lower section 34 and an upper section 36. The upper section 36 is smaller than the lower section 34.

A spring clip 24 is mounted on each post 30. Only one of the spring clips 24 is shown and described with the understanding that the other spring clips 24 are identical in structure and in function.

Figure 2:
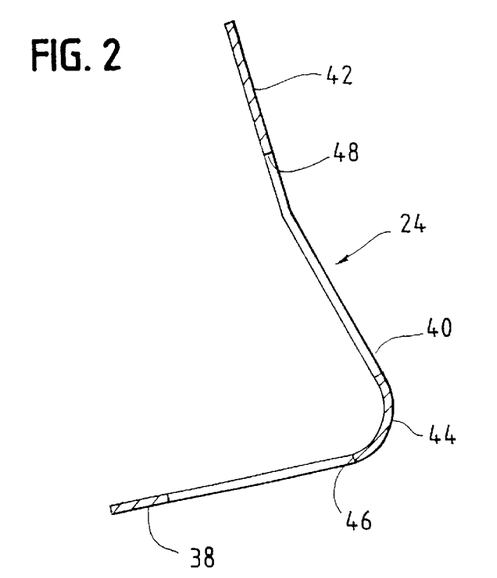
FIG. 2 is a side view of a clip which is used in the present invention.

The spring clip 24 is formed of carbon steel. As best shown in FIG. 2, the spring clip 24 is integrally formed from a lower portion 38, an intermediate portion 40 and an upper portion 42, with the intermediate portion 40 being between and joining the lower portion 38 and the upper portion 42. The lower portion 38 and the intermediate portion 40 are angled relative to each other, approximately 70°. The joint 44 between the lower portion 38 and the intermediate portion 40 may be rounded as shown in the drawings. The upper portion 42 is angled relative to the intermediate portion 40, approximately 15°, and is angled relative to the lower portion 38, approximately 85°.

A lower aperture 46 is provided through the lower portion 38 of the spring clip 24. The lower aperture 46 is provided through the lower portion 38 at a distance spaced from the lower end of the spring clip 24 and spaced from the joint 44. An upper aperture 48 is provided through a lower section of the upper portion 42 and an upper section of the intermediate portion 40 of the spring clip 24. The upper aperture 48 is provided at a distance spaced from the upper end of the spring clip 24 and spaced from the joint 44. Each aperture 46, 48 is generally rectangular.

Figure 1:
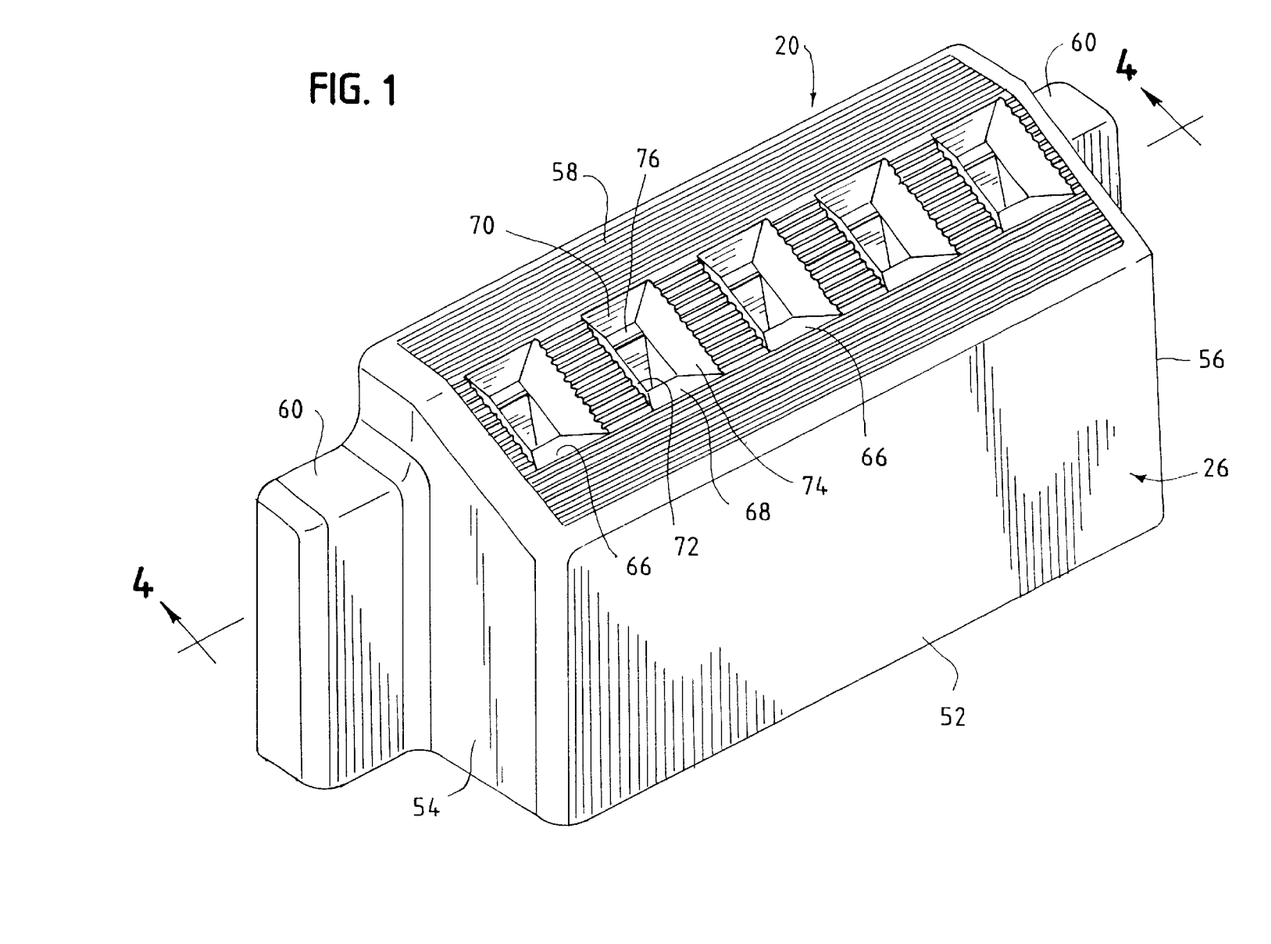
FIG. 1 is a perspective of a device which incorporates the features of a first embodiment of the present invention.

As shown in FIG. 1, the upper member 26 is formed of a suitable material, such as plastic. The upper member 26 is integrally formed and includes opposing side walls 50, 52 and opposing end walls 54, 56, such that a rectangular cross-section is formed, and a top wall 58. The bottom of the upper member 26 is open. Each side wall 50, 52 has a recess therein, proximate to the bottom end thereof, which extends substantially the entire length thereof. An ear or protrusion 60 is provided on each end wall 54, 56 and protrudes outwardly therefrom. As shown in the drawings, each ear 60 has a height which may be less than the height of the respective end wall 54, 56.

The top wall 58 is provided at the upper end of the side walls 50, 52 and the end walls 54, 56. An upper portion 62 of the top wall 58 is perpendicular to the side walls 50, 52 and the end walls 54, 56, and a lower portion 64 of the top wall 58 is angled relative to the side walls 50, 52 and the end walls 54, 56.

A plurality of needle receiving apertures 66 are provided through the lower portion 64 of the top wall 58 and are spaced apart from each other. Each aperture 66 includes opposite side walls 68, 70 and opposite end walls 72, 74 which extend downwardly from the lower portion 64 of the top wall 58. The side walls 68, 70 angle inwardly toward each other and are angled relative to the lower portion 64 of the top wall 58. The end walls 72, 74 angle inwardly toward each other and are angled relative to the lower portion 64 of the top wall 58. A flange 76, see FIGS. 4–7, protrudes from a bottom end of the side wall 70 and is parallel to the lower portion 64 of the top wall 58. A reduced portion 78 of the needle receiving aperture 66 is defined by the bottom end of the side wall 68, the bottom end of the end walls 72, 74, and the inner end of the flange 76. As such, a funnel-like guide path is provided through the lower portion 64 of the top wall 58 of the upper member 26.

A plurality of recesses 80 are provided in the underside of the lower portion 64 of the top wall 58, see FIGS. 4–7. Each recess 80 is respectively provided at a position which is spaced from the side wall 52 and from the needle receiving aperture 66.

To assemble the device 20, a spring clip 24 is mounted on each post 30 by inserting the post 30 through the lower aperture 46 and then through the upper aperture 48 of the spring clip 24. The spring clip 24 secures itself to the post 30 by spring force. The assembly of the respective spring clips 24 with the respective posts 30 form a lower assembly. The lower assembly is inserted through the open bottom end of the upper member 26 until the ribs 32 on the base 28 engage within the recesses on the side walls 50, 52 of the upper member 26. This engagement holds the upper member 26 and the lower assembly together. The upper portion 36 of each post 30 engages within the respective recess 80 in the lower portion 64 of the top wall 58. The upper portion 42 of each spring clip 24 extends across and substantially covers the respective needle receiving aperture 66.

The ears 60 provided on the end walls 54, 56 of the device 20 releasably lock with restraining features in a vacuum formed kit tray so the device 20 will remain upright when loaded and in place until pulled out of the tray for disposal.

When the needle 82 is inserted into the device 20, the needle 82 is naturally guided into the crotch formed between the post 30 and the spring clip 24 by the funnel-like guide path formed by the needle receiving aperture 66 in the upper member 26. This causes the upper portion 42 of the spring clip 24 to lift off of the post 30 and to permit entry of the needle 82 into the upper aperture 48, thereby trapping the needle 82 between the upper portion 42 of the spring clip 24 and the post 30. The spring force of the spring clip 24 causes the sharp corner of the upper edge of the upper aperture 48 to bite into the softer needle material (the needle 82 is made of stainless steel). The angling of the upper portion 42 relative to the intermediate portion 40 by 15° serves to provide better rake on the biting edge for enhanced biting or digging into the needle 82.

Figure 12:
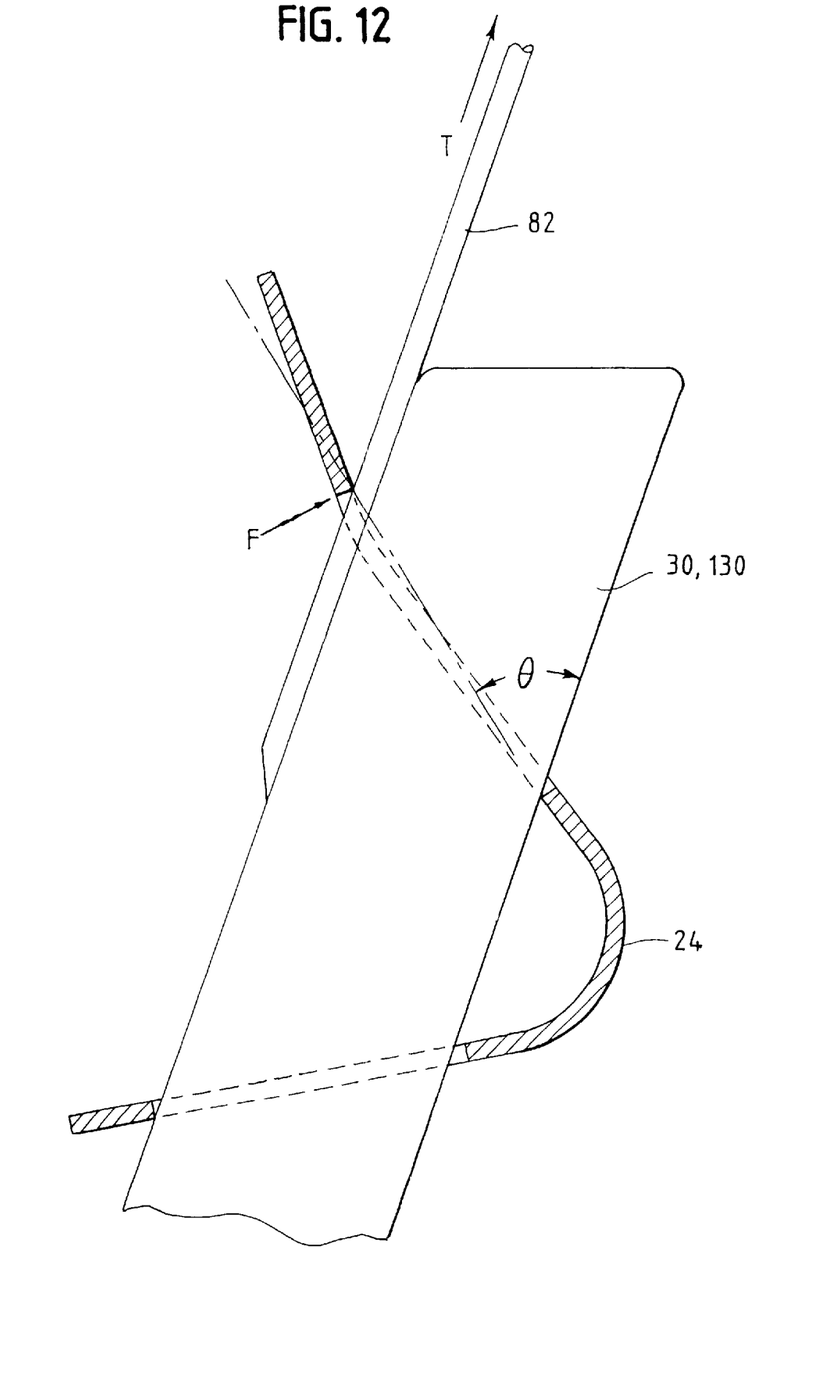
FIG. 12 is a partial side elevational view of a post and a needle and a cross-sectional view of a clip mounted thereon.

Attempts to withdraw the needle 82 causes the spring clip 24 to pivot about the point where the lower edge of the upper aperture 48 engages the post 30, pulling the needle 82 more tightly against the post 30 and causing the upper edge of the upper aperture 48 to bite more securely into the needle 82. The needle 82 may be pushed further into the device 20, but the needle 82 cannot be pulled out of the device 20. As shown in FIG. 12, as a longitudinal tension force T is exerted to extract the inserted needle 82, tension results on the clip 24. This tension on the clip 24, as a result of reaction of the clip 24, increases the transverse biting force F of the clip 24 against the needle 82. This enhances the grip upon the needle 82 by the clip 24 in order to prevent the needle 82 from being withdrawn by the longitudinal tension force T. $\ominus$ is the swung arc from the intersection of the clip 24 with the needle 82 and the opposite side of the post 30 and $F=\sin\ominus \times T$.

Attention is invited to the second embodiment of the invention shown in FIGS. 6 and 7. This second embodiment of the device 20' includes an audible indicator feature. The lower member 22' and the upper member 26' are identical to that as shown in FIGS. 3–5. The spring clip 24' is identical to the spring clip 24 of the first embodiment, except that the upper aperture 48a' is longer in length than the upper aperture 48 shown in FIGS. 3–5 so that a needle pocket 84 is accommodated between the upper portion 42' of the spring clip 24' and the post 30'. Like elements in the first and second embodiments are labeled with like reference numbers with the elements in the second embodiment having a prime after the reference number.

The needle pocket 84 is formed of a suitable material, such as plastic. The needle pocket 84 includes a housing 88 which includes a recess 90 therein which extends inwardly from a top end of the housing 88.

To assemble the device 20', a needle pocket 84 is held on each post 30'. A spring clip 24' is then mounted on each post 30' by inserting the post 30' through the lower aperture 46' and then through the upper aperture 48a'. The housing 88 is positioned within the upper aperture 48a' such that the needle pocket 84 is between the upper portion 42' of the spring clip 24' and the post 30' and the open end of the recess 90 faces the needle receiving aperture 66'. The spring clip 24' secures itself by spring force to the post 30' and to the needle pocket 84. The assembly of the needle pockets 84 and the spring clips 24' with the respective posts 30' form a lower assembly. The lower assembly is inserted through the bottom end of the upper member 26' until the ribs 32' engage within the recesses. This engagement holds the upper member 26' and the lower assembly together. The upper portion 36' of each post 30' engages within the respective recess 80' in the lower portion 64' of the top wall 58'. The upper portion 42' of each spring clip 24' extends across and substantially covers the respective needle receiving apertures 66'.

When the needle 82 is inserted into the device 20', the needle 82 is naturally guided into the recess 90 within the needle pocket 84 by the funnel-like guide path formed by the needle receiving aperture 66' in the upper member 26'. Upon sufficient downward movement, the needle pocket 84 is moved from engagement between the spring clip 24' and the post 30'. This causes the spring clip 24' to slap against the needle 82 (which has a diameter which is less than the thickness of the needle pocket 84), thereby trapping the needle 82 between the upper portion 42' of the spring clip 24' and the post 30'. The slapping of the spring clip 24' against the needle 82 provides an audible "snap" to indicate the needle 82 is secure. It is believed that this slapping of the spring clip 24' also dents into the needle 82, thereby enhancing the bite of the spring clip 24' into the needle 82. The spring force of the spring clip 24' causes the sharp corner of the upper edge of the upper aperture 48a' to bite into the softer needle material. The angling of the upper portion 42' relative to the intermediate portion 40 by 15° serves to provide better rake on the biting edge for enhanced biting or digging into the needle 82.

Attempts to withdraw the needle 82 causes the spring clip 24' to pivot about the point where the lower edge of the upper aperture 48a' engages the post 30', pulling the needle 82 more tightly against the post 30' and causing the lower edge of the upper aperture 48a' to bite more securely into the needle 82. The needle 82 may be pushed further into the device 20', but the needle 82 cannot be pulled out of the device 20'. As shown in FIG. 12, as a longitudinal tension force T is exerted to extract the inserted needle 82, tension results on the clip 24. This tension on the clip 24, as a result of reaction of the clip 24, increases the transverse biting force F of the clip 24 against the needle 82. This enhances the grip upon the needle 82 by the clip 24 in order to prevent the needle 82 from being withdrawn by the longitudinal tension force T. $\ominus$ is the swung arc from the intersection of the clip 24 with the needle 82 and the opposite side of the post 30 and $F=\sin\ominus \times T$.

In the first and second embodiments, the elongated ribs 32, 32' can be provided on the side walls 50, 52 of the upper member 26 and the recesses can be provided in the base 28 to provide the mating action.

Attention is invited to the third, and preferred, embodiment of the invention shown in FIGS. 8–11. The device 20" includes a lower member 122, a plurality of spring clips 24 and an upper member 126. The lower and upper members 122, 126 form a housing when coupled together.

Figures 8, 9:
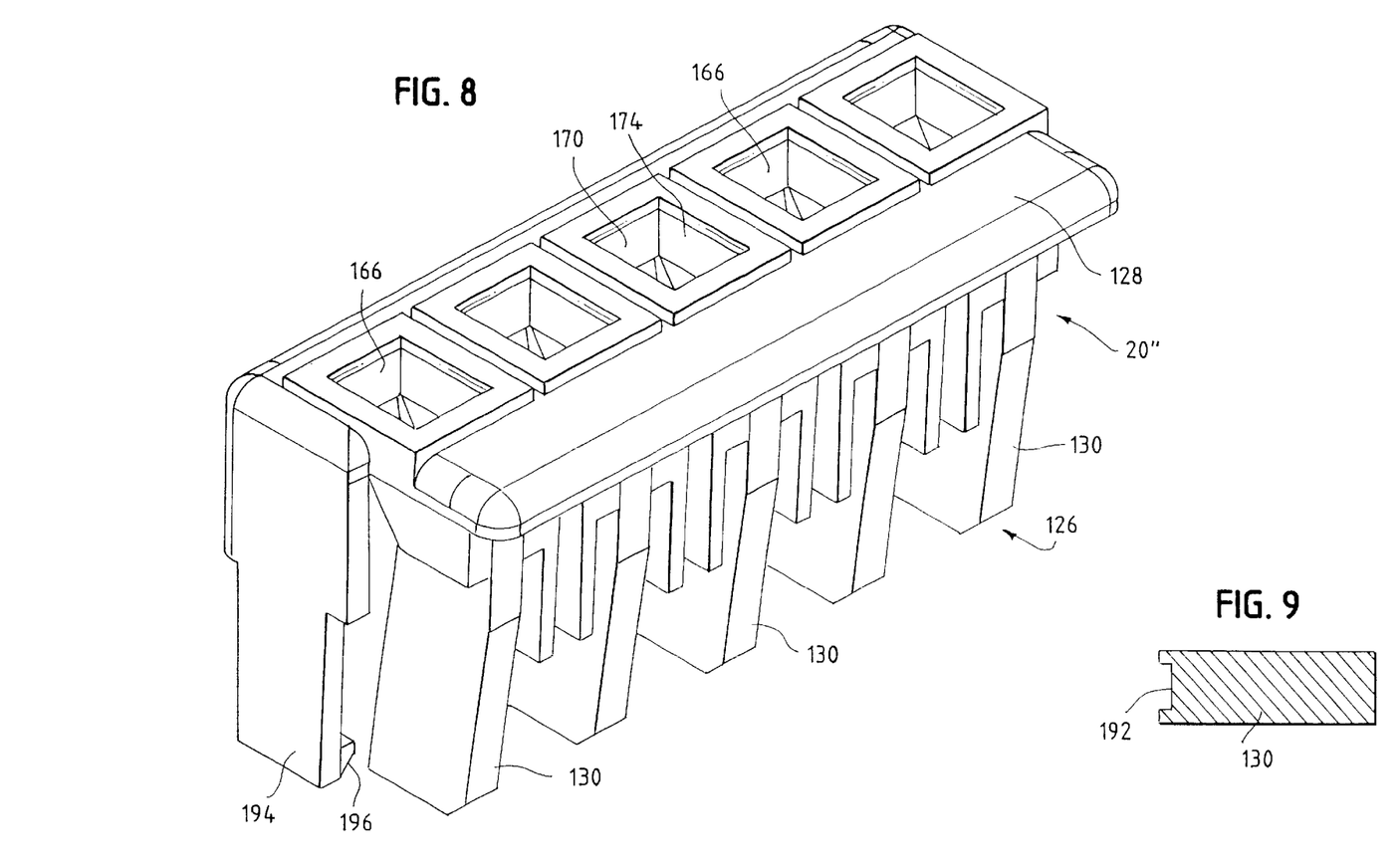
FIG. 8 is a perspective view of an upper member of a third embodiment of the invention which includes a plurality of posts.
FIG. 9 is a perspective view of a lower member of the third embodiment of the invention.

As shown in FIG. 8, the upper member 126 is integrally formed of a suitable material, such as plastic. The upper member 126 includes a horizontal base 128 and a plurality of generally rectangular posts 130 which depend therefrom.

The posts 130 extend downwardly from the base 128 and are spaced apart from each other along the length of the base 128. As shown in the drawings, the base 128 is rectangular and five posts 130 are provided thereon. Each post 130 extends downwardly from the base 128 at an angle relative thereto. Each post 130 is preferably 0.060 inches wide.

The base 128 includes a plurality of needle receiving apertures 166 provided therethrough. The needle receiving apertures 166 are spaced apart from each other and are respectively aligned with the posts 130, but are offset from the posts 130. Each aperture 166 includes opposite side walls 168, 170, see FIGS. 8 and 11, and opposite end walls 174, only one shown in FIG. 8, which extend downwardly from the base 128. The side walls 168, 170 angle inwardly toward each other and are angled relative to the base 128. The end walls 174 angle inwardly toward each other and are angled relative to the base 128. A reduced portion 178 of the needle receiving aperture 166 is defined by the bottom ends of the side walls 168, 170 and the bottom ends of the end walls 174. As such, a funnel-like guide path is provided through the base 128.

Figure 11:
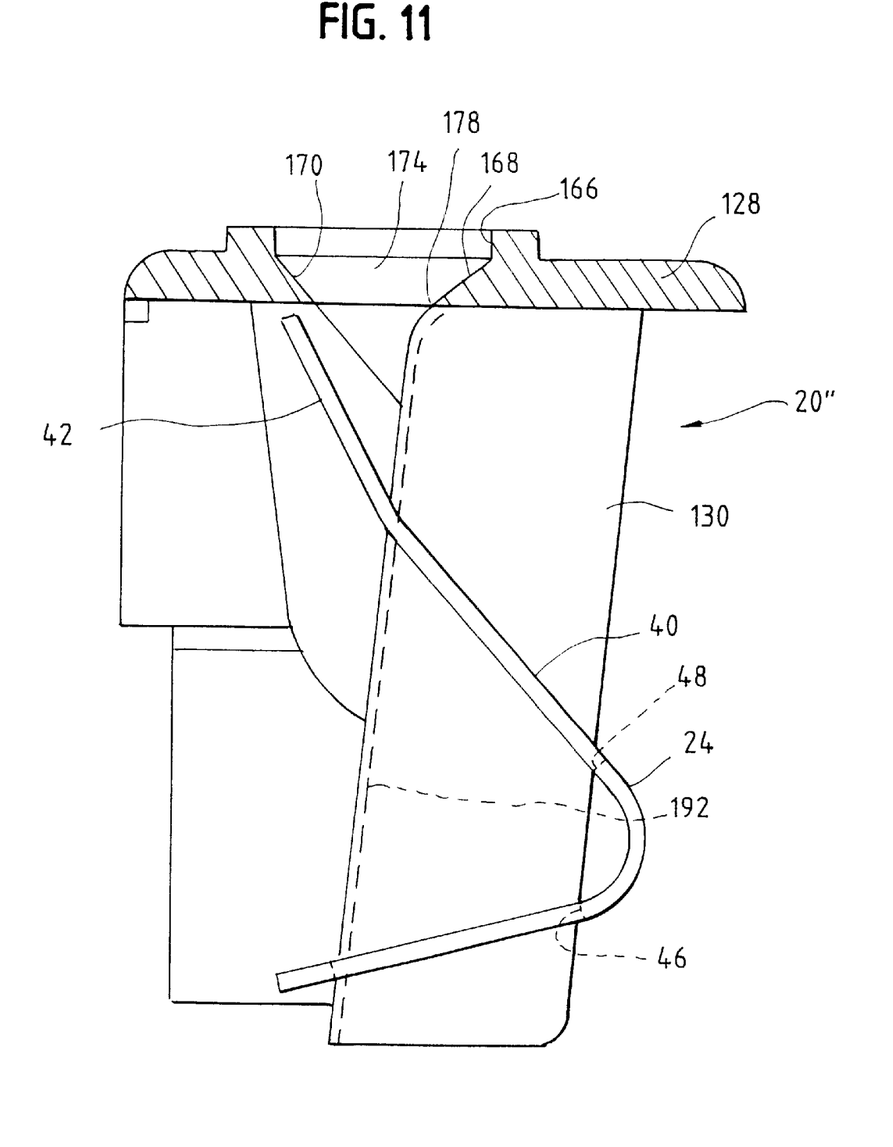
FIG. 11 is a cross-sectional view of a post of device shown in FIG. 8.

A groove 192, see FIGS. 9 and 11, is provided along the length of each post 130. The groove 192 is provided in the surface of each post 130 proximate to the respective needle receiving aperture 166. The groove 192 is preferably 0.038 inches to 0.040 inches wide and centered on the post 130. The groove 192 is preferably 0.006 inches deep.

An arm 194 depends from each end of the base 128 in the same direction as the posts 130. The arms 194 are spaced from the endmost posts 130. A barb 196 is provided at the end of each arm 194 and is perpendicular to the respective arm 194. Each barb 196 extends toward the posts 130.

A spring clip 24" is mounted on each post 130. Only one of the spring clips 24", see FIG. 11, is shown and described with the understanding that the other spring clips 24" are identical in structure and in function. The spring clip 24" is identical to the spring clip 24 of the first embodiment. Like elements of the spring clip 24" in the first and third embodiments are labeled with like reference numbers with the elements in the third embodiment having a double prime after the reference number.

Figure 10:
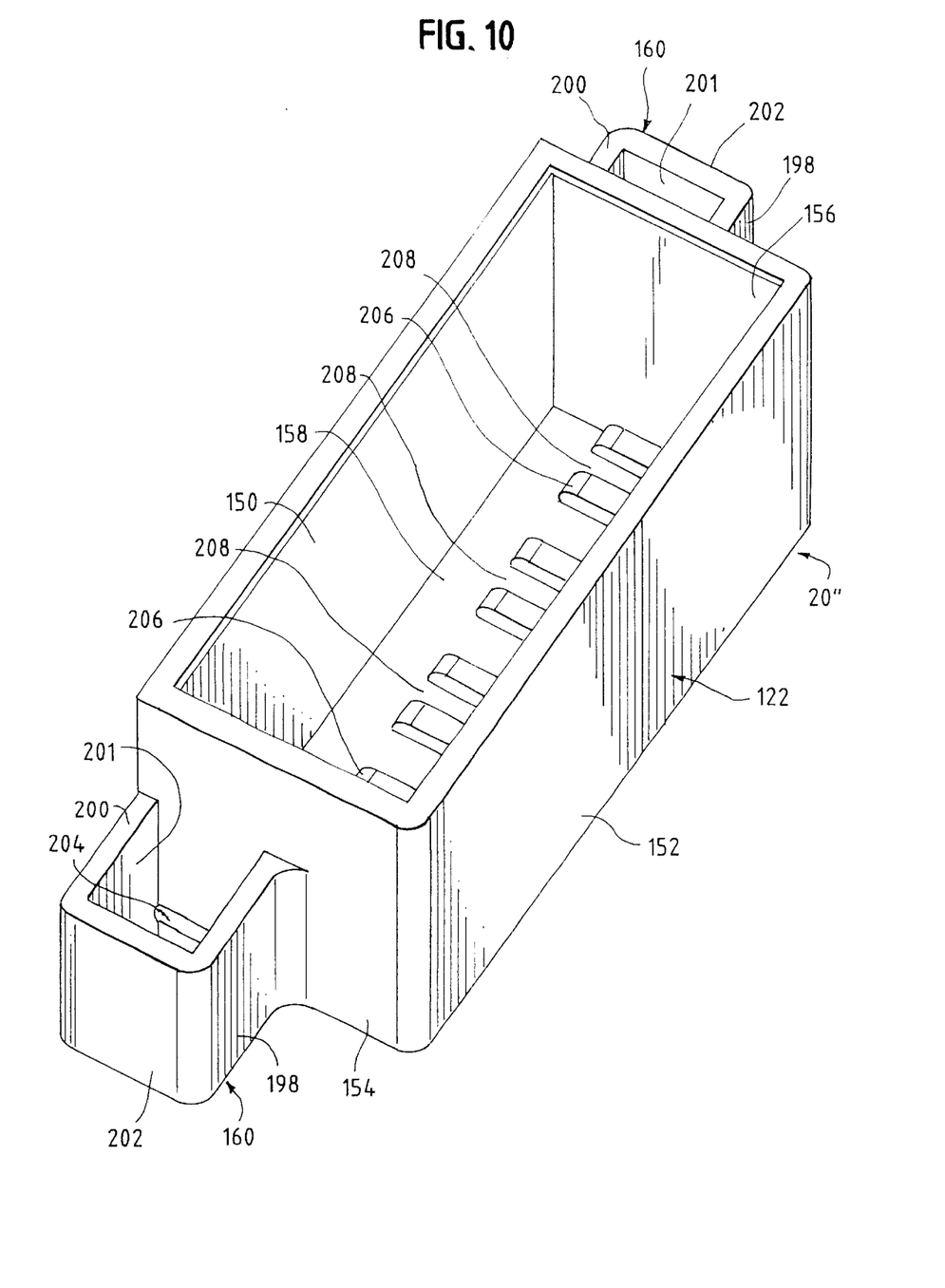
FIG. 10 is a cross-sectional view of the upper portion shown in FIG. 8 which has a clip mounted thereon.

As shown in FIG. 10, the lower member 122 is formed of a suitable material, such as plastic. The lower member 122 includes opposing side walls 150, 152 and opposing end walls 154, 156, such that a rectangular cross-section is formed, and a bottom wall 158. The upper end of the lower member 122 is open.

Each end wall 154, 156 has an ear 160 attached thereto. Each ear 160 is formed of a pair of side walls 198, 200 which extend perpendicularly from the respective end wall 154, 156, and an end wall 202 which is attached to the opposite ends of the side walls 198, 200. A passageway 201 is provided through each ear 160. A retaining barb 204 is provided on each end wall 154, 156 and mates with the respective barb 196 on the arm 194 of the upper member 126 when the upper member 126 and the lower member 122 are mated together.

The bottom wall 158 has a plurality of protrusions 206 provided thereon and extending upwardly therefrom. The protrusions 206 are spaced apart from each other along the length of the bottom wall 158. The protrusion 206 are spaced such that pockets 208 are formed between adjacent protrusions 206. Only three of the five pockets 208 are shown in FIG. 10.

To assemble the device 20", a spring clip 24 is mounted on each post 130 by inserting the post 130 through the upper aperture 48 and then through the lower aperture 46 of the spring clip 24. The spring clip 24 secures itself to the post 130 by spring force. The assembly of the respective spring clips 24 with the respective posts 130 form an upper assembly. The upper assembly is inserted through the open upper end of the lower member 122 until the barbs 196 on the arms 194 snap over and engage with the barbs 204 in the ears 160. This engagement holds the lower member 122 and the upper assembly together. The lower portion of each post 130 engages within the respective pocket 208 on the bottom wall 158 of the lower member 122. The upper portion 42 of each spring clip 24 extends across and substantially covers the respective needle receiving aperture 166.

The arms 194 do not completely fill the passageway 201 in the ears 160. This allows the ears 160 to releasably lock with restraining features in a vacuum formed kit tray so the device 20" will remain upright when loaded and in place until pulled out of the tray for disposal.

When the needle 82 is inserted into the device 20", the needle 82 is naturally guided into the crotch formed between the post 130 and the spring clip 24 by the funnel-like guide path formed by the needle receiving aperture 166 in the upper member 126. The needle 82 enters into the groove 192 formed in the post 130. When the needle 82 engages the spring clip 24, the upper portion 42 of the spring clip 24 lifts off of the post 130 and permits entry of the needle 82 into and through the upper aperture 48, thereby trapping the needle 82 between the upper portion 42 of the spring clip 24 and the post 130. The groove 192 assists in entry of the needle 82 and reduces the required insertion force. In addition, the groove 192 aids in keeping the needle 82 aligned with the post 130. The spring force of the spring clip 24 causes the sharp corner of the upper edge of the upper aperture 48 to bite into the softer needle material (the needle 82 is made of stainless steel). The angling of the upper portion 42 relative to the intermediate portion 40 by 15° serves to provide better rake on the biting edge for enhanced biting or digging into the needle 82.

Attempts to withdraw the needle 82 causes the spring clip 24 to pivot about the point where the lower edge of the upper aperture 48 engages the post 130, pulling the needle 82 more tightly against the post 130 and causing the upper edge of the upper aperture 48 to bite more securely into the needle 82. The needle 82 may be pushed further into the device 20", but the needle 82 cannot be pulled out of the device 20". As shown in FIG. 12, as a longitudinal tension force T is exerted to extract the inserted needle 82, tension results on the clip 24. This tension on the clip 24, as a result of reaction of the clip 24, increases the transverse biting force F of the clip 24 against the needle 82. This enhances the grip upon the needle 82 by the clip 24 in order to prevent the needle 82 from being withdrawn by the longitudinal tension force T. $\Theta$ is the swung arc from the intersection of the clip 24 with the needle 82 and the opposite side of the post 130 and $F=\sin\Theta \times T$.

The third and preferred embodiment of the device 20" provides a joint free, fluid-containing tub like form. This allows the lower member 122 of the device 20" to contain any small fluid droplets that might exude from an inserted needle 82 without fear of a leak from a low placed joint like that shown in the first and second embodiments of the device 20, 20'.

In this third embodiment, the barb 196 on the arm 194 could protrude from the other side of the arm 194 and the barb 204 on the lower member 122 would be provided on end wall 202 to provide for the mating action. In addition, in this third embodiment, the arms 194 could be provided on the lower member 122 and the ears 160 provided on the upper member 126.

In each embodiment, the spring clip 24 is harder than the hardest needle 82 it will encounter. If the device 20, 20', 20" is to be used with larger diameter needles which have a hardness of 375 BHN, the spring clip 24 used in the present invention can be formed of spring steel having a hardness of 48C Rockwell. If the device 20, 20', 20" is to be used with smaller diameter needles, because smaller diameter needles receive more work hardening and thus end up harder at 415 BHN than a larger diameter needle, the spring clip 24 used in the present invention is heat treated to harden the spring clip 24 preferably to 55C Rockwell to 60C Rockwell. Preferably, only the portion of the spring clip 24 which bites into the needle 82 is hardened by local heat treating. It has been found that if the whole spring clip 24 is hardened, the spring clip 24 becomes too brittle if the device 20, 20', 20" is used with larger diameter needles.

It is to be understood that while the groove 192 is shown and described with respect to the third embodiment of the device 20", the groove 192 can be provided on the posts 30, 30' of the device 20, 20' of the first or second embodiments.

It is to be understood that while the posts 30, 30', 130 are shown and described as angled relative to the base wall 28, 28', 128, the posts 30, 30', 130 could be perpendicular to the base 28, 28', 128. The angling of the posts 30, 30', 130 keeps the overall assembly height down and also serves to "aim" the needle receiving apertures 66, 66', 166 more naturally toward the user.

While the device 20, 20', 20" is shown in the drawings with five needle receiving apertures 66, 66', 166 the device 20, 20', 20" can be made to accommodate any number of needles 82 from one to a dozen or more if required. Obviously, not all of the needle receiving apertures 66, 66', 166 need to be used for the device 20, 20', 20" to function.

In addition, the base 28, 28', 128 may take other shapes, such as a square, and is not limited to the shape shown in the drawings.

While preferred embodiments of the present invention are shown and described, it is envisioned that those skilled in the art may devise various modifications of the present invention without departing from the spirit and scope of the appended claims.

The invention claimed is:

1. A needle immobilization safety device comprising:
a housing, said housing having an aperture therethrough for acceptance of a needle therethrough;
a post provided within said housing and provided proximate to said aperture; and
a clip mounted on said post, said clip being capable of being moved away from said post when the needle is inserted into said housing, and said clip further being capable of biting into the needle as the needle passes between said clip and said post.

2. A needle immobilization safety device as defined in claim 1, wherein said housing includes an upper member, a lower member and joining means for joining said upper and lower members together.

3. A needle immobilization safety device as defined in claim 2, wherein said post is provided on said upper member.

4. A needle immobilization safety device as defined in claim 3, wherein said post is angled relative to said upper member.

5. A needle immobilization safety device as defined in claim 2, wherein said post is provided on said lower member.

6. A needle immobilization safety device as defined in claim 5, wherein said post is angled relative to said lower member.

7. A needle immobilization safety device as defined in claim 5, wherein said upper member includes a recess therein, and wherein an upper end of said post is inserted within said recess when said upper and lower portions are assembled together.

8. A needle immobilization safety device as defined in claim 1, wherein said post is elongated and includes a groove along a length of said post, said clip laying over said groove.

9. A needle immobilization safety device as defined in claim 1, wherein said clip is formed from spring steel.

10. A needle immobilization safety device as defined in claim 9, wherein said clip has a hardness of 48C Rockwell.

11. A needle immobilization safety device as defined in claim 9, wherein said clip is heat treated to harden said spring clip to 55C Rockwell to 60C Rockwell.

12. A needle immobilization safety device as defined in claim 1, wherein said aperture is formed through a base wall of said housing, said aperture being defined by aperture walls which are angled relative to said base wall.

13. A needle immobilization safety device as defined in claim 1, further including a member having a recess therein for receiving the needle, said member being provided between said clip and said post prior to insertion of the needle and being moved from between said clip and said post during insertion of the needle.

14. A needle immobilization safety device comprising:
a housing, said housing having an aperture therethrough for acceptance of a needle therethrough, said housing including an upper member, a lower member and joining means for joining said upper and lower members together, said joining means comprising at least one arm attached to one of said upper and lower members, said at least one arm having a first barb provided thereon, and a second barb formed on the other of said upper and lower members;
a post provided within said housing and provided proximate to said aperture; and
a clip mounted on said post, said clip being capable of being moved away from said post when the needle is inserted into said housing, and said clip further being capable of biting into the needle as the needle passes between said clip and said post.

15. A needle immobilization safety device comprising:
a housing, said housing having an aperture therethrough for acceptance of a needle therethrough, said housing including an upper member, a lower member and joining means for joining said upper and lower members together;
a post provided within said housing on said upper member and provided proximate to said aperture; and
a clip mounted on said post, said clip being capable of being moved away from said post when the needle is inserted into said housing, and said clip is further being capable of biting into the needle as the needle passes between said clip and said post,
said lower member including a pair of spaced apart protrusions, said post being inserted between said protrusions when said upper and lower portions are assembled together.

16. A needle immobilization safety device comprising:
a housing, said housing having an aperture therethrough for acceptance of a needle therethrough;
a post provided within said housing and provided proximate to said aperture; and
a clip mounted on said post, said clip being capable of being moved away from said post when the needle is inserted into said housing, and said clip further being capable of biting into the needle as the needle passes between said clip and said post, said clip including a lower portion, an intermediate portion, and an upper portion, said post extending through said lower portion and said upper portion.

17. A needle immobilization safety device as defined in claim 16, wherein said lower portion and said intermediate portion are angled relative to each other.

18. A needle immobilization safety device as defined in claim 17, wherein said lower portion and said intermediate portion are angled relative to each other by approximately 70°.

19. A needle immobilization safety device as defined in claim 16, wherein said upper portion and said intermediate portion are angled relative to each other.

20. A needle immobilization safety device as defined in claim 19, wherein said upper portion and said intermediate portion are angled relative to each other by approximately 15°.

21. A needle immobilization safety device as defined in claim 20, wherein said upper portion and said lower portion are angled relative to each other by approximately 85°.

22. A needle immobilization safety device comprising:
   a housing, said housing having an aperture therethrough for acceptance of a needle therethrough, said housing including at least one ear extending therefrom for attachment to an associated tray;
   a post provided within said housing and provided proximate to said aperture; and
   a clip mounted on said post, said clip being capable of being moved away from said post when the needle is inserted into said housing, and said clip further being capable of biting into the needle as the needle passes between said clip and said post.

23. A needle immobilization safety device comprising:
   an upper member, said upper member having an aperture therethrough for acceptance of a needle therethrough;
   a lower member;
   joining means for joining said upper and lower members together;
   at least one ear extending from one of said upper or lower members for attachment to an associated tray;
   a post provided on one of said upper and lower members and provided proximate to said aperture; and
   a clip mounted on said post, said clip being capable of being moved away from said post when the needle is inserted into said housing, and said clip further being capable of biting into the needle as the needle passes between said clip and said post.

24. A needle immobilization safety device as defined in claim 23, wherein said joining means comprises at least one arm attached to one of said upper and lower members, said at least one arm having a first barb provided thereon;
   a second barb formed on the other of said upper and lower members for mating with said first barb.

25. A needle immobilization safety device as defined in claim 23, wherein said post is elongated and includes a groove along a length of said post, said clip laying over said groove.

26. A needle immobilization safety device as defined in claim 23, wherein said clip includes an upper portion and a lower portion, said upper portion and said lower portion being angled relative to each other, said post passing through said upper portion and said lower portion.

27. A needle immobilization safety device as defined in claim 23, wherein said post is provided on said upper member and said lower member includes a pair of spaced apart protrusions, said post being inserted between said protrusion when said upper and lower portions are assembled together.

28. A needle immobilization safety device comprising:
   a housing, said housing having at least one aperture therethrough for acceptance of associated needles therethrough;
   a plurality of posts provided within said housing and provided proximate to said at least one aperture; and
   a clip mounted on each said post, each said clip being capable of being moved away from said respective post when the respective needle is inserted into said housing, and each said clip further being capable of biting into the respective needle as the respective needle passes between said clip and said post.

29. A needle immobilization safety device as defined in claim 28, wherein said housing includes an upper member, a lower member and joining means for joining said upper and lower members together.

30. A needle immobilization safety device as defined in claim 29, wherein said joining means comprises at least one arm attached to one of said upper and lower members, said at least one arm having a first barb provided thereon, and a second barb formed on the other of said upper and lower members.

31. A needle immobilization safety device as defined in claim 29, wherein said plurality of posts are provided on said upper member.

32. A needle immobilization safety device as defined in claim 29, wherein said plurality of posts are provided on said lower member.

33. A needle immobilization safety device as defined in claim 28, wherein each said post is elongated and includes a groove along a length of said post, said clip laying over said groove.

34. A needle immobilization safety device as defined in claim 28, wherein each said clip is formed from spring steel.

35. A needle immobilization safety device as defined in claim 28, wherein said housing includes at least one ear extending therefrom for attachment to an associated tray.

36. A needle immobilization safety device as defined in claim 28, further including a plurality of members, each said member having a recess therein for receiving the respective needle, each said member being provided between said respective clip and said respective post prior to insertion of the respective needle and being moved from between said clip and said post during insertion of the needle.

37. A method of immobilizing a needle comprising the steps of:
   providing a needle immobilization safety device including a housing, said housing having an aperture therethrough for acceptance of a needle therethrough, a post provided within said housing and provided proximate to said aperture, and a clip mounted on said post;
   inserting said needle into said housing;
   inserting said needle between said post and said clip, said clip moving away from said post; and
   said clip biting into said needle and exerting a biting force on said needle as said needle passes between said clip and said post.

38. A method as defined in claim 37, wherein longitudinal tension force exerted to extract said inserted needle results in tension upon said clip which tension, by reaction of said clip, increases said biting force of said clip against said needle.

* * * * *